United States Patent [19]

Walser et al.

[11] Patent Number: 5,317,018

[45] Date of Patent: May 31, 1994

[54] BENZODIAZEPINES AND COMPOSITIONS FOR TREATING ANXIETY AND PANIC DISORDERS, AND IDIOPATHIC AND PSYCHOMOTOR EPILEPSY

[76] Inventors: Armin Walser, 19 Crane Ave., West Caldwell, N.J. 07006; Alessandro Guidotti, 4434 Macomb St., NW., Washington, D.C. 20016; Erminio Costa, 6001 Brookside Dr., Chevy Chase, Md. 20815

[21] Appl. No.: 895,851

[22] Filed: Jun. 9, 1992

[51] Int. Cl.$^5$ .................. A61K 31/55; C07D 487/04
[52] U.S. Cl. .................................. 514/220; 540/562
[58] Field of Search .................. 540/562; 514/220

[56] References Cited

U.S. PATENT DOCUMENTS 4,280,957  7/1981  Walser et al. ............... 260/244.4

FOREIGN PATENT DOCUMENTS 0109921  5/1984  European Pat. Off. .
0135770  4/1985  European Pat. Off. .
0451626  10/1991  European Pat. Off. .
0488044  6/1992  European Pat. Off. .
2813549  10/1978  Fed. Rep. of Germany .

OTHER PUBLICATIONS

The Journal of Pharm. and Exp. Ther., vol. 257, No. 3, (1991), pp. 1062-1068 The Preferential Antagonism of Pentylenetetrazole Proconflict Responses Differentiates a Class of Anxiolytic Benzodiazepines with Potential Antipanic Action, Giusti et al.
The Benzodiazepines: From Molecular Biology to Clinical Practice, J. Overweg et al., Benzodiazepines in Neurological Disorders, (1983) pp. 339-347.
The Benzodiazepines: From Molecular Biology to Clinical Practice, W. Haefely et al., Neuropharmacology of Benzodiazepines: Synaptic Mechanism and ... , pp. 21-66 (1983).
Watjen et al., Chemical Abstract vol. 111, No. 153763m (1989).

*Primary Examiner*—John M. Ford
*Assistant Examiner*—Philip I. Datlow

[57] ABSTRACT

The present invention is directed to imidazo[1,5-a][1,4]benzodiazepine-3-carboxamide compounds of the formula:

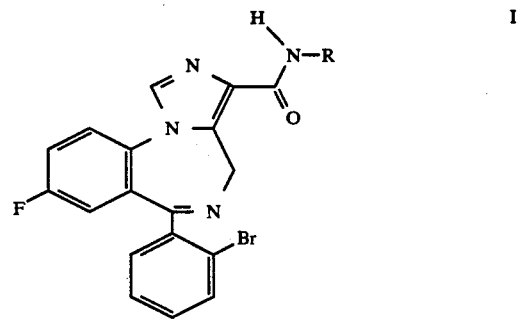

wherein R is hydrogen, $C_3CH_2-$, $CH_2=CHCH_2-$, $(CH_3)_2CH-$, $CH_3CH_2CH_2-$, or

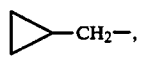

or a pharmaceutically acceptable salt thereof. These compounds and their pharmaceutically acceptable salts possess anti-anxiety and anti-epileptic activity.

24 Claims, 1 Drawing Sheet

BENZODIAZEPINES AND COMPOSITIONS FOR TREATING ANXIETY AND PANIC DISORDERS, AND IDIOPATHIC AND PSYCHOMOTOR EPILEPSY

BACKGROUND OF THE INVENTION

Anxiety Disorders

Although traditional benzodiazepines (BZDs) and their congeners have been the drugs of choice for the relief of generalized anxiety for over 30 years, they have not been used in the treatment of panic disorders. Recently, it has been generally reported that the so-called "high potency" BZDs (alprazolam, clonazepam, bretazenil) can be differentiated from traditional BZD's in experiments which indicate the potential of a drug to be effective as an antipanic agent. Giusti et al., J. Pharmacol. Exper. Therapeutics 257:1062–68 (1991).

The Diagnostic and Statistical Manual of Mental Disorders, 3rd edition (DMS III) (1980), divides anxiety/neurosis into the following subtypes: generalized anxiety, panic disorders, and obsessive-compulsive disorders. Although numerous behavioral procedures are used successfully to predict the action of drugs on generalized anxiety, a comparable behavioral model for the study of drugs active on panic disorders and obsessive behaviors has been lacking. A simple behavioral test in rats that predicts the antipanic potency of drugs acting on GABA receptors has been developed. In this test, the acute punished suppression of the drinking paradigm in thirsty rats (Vogel test) was used to discriminate between diazepam, zolpidem, alpidem, and midazolam, which are low potency BZDs with anxiolytic properties, and alprazolam, clonazepam, and bretazenil, which are high potency BZDs effective in the treatment of panic disorders. The Vogel test, in its conflict paradigm, can be used in animals to ascertain the potential anxiolytic or anxiety producing properties of drugs. When the Vogel test is used in conjunction with pentylenetetrazole (PTZ) treatment it is called "proconflict test" and can be used to ascertain the antipanic potential of drugs PTZ has been used to decrease $GABA_A$ receptor function and therefore to make the Vogel test more sensitive to antipanic BZD drugs.

In man, subconvulsant doses of PTZ produce intense anxiety and sense of impending doom, a behavioral syndrome reminiscent of a panic attack. Thus, the Vogel test in both conflict and proconflict (PTZ-facilitated conflict) paradigms is used as an animal model to evaluate the $GABA_A$ receptor contribution to the action of drugs that decrease response suppression. When a series of BZDs and their congeners are evaluated in the proconflict paradigm, it is found that the potencies and efficacies of the antipanic BZDs alprazolam, clonazepam, and bretazenil surpassed those of the anxiolytic BZD ligands diazepam, zolpidem, alpidem, and midazolam.

Diazepam, midazolam, alpidem, and zolpidem antagonized the conflict and proconflict responses in a dose-dependent manner with similar potencies and efficacies, yielding anti-proconflict indexes close to 1. On the other hand, the 1,4-BZD clonazepam, the triazolo 1,4-BZD alprazolam, and the imidazo 1,4-BZD bretazenil also increased the threshold for the conflict behavior in a dose-dependent manner, but they were significantly more potent in antagonizing the proconflict effect elicited by PTZ. These drugs yielded anti-proconflict indexes close to 10. Because there was no correlation between the anti-proconflict index values and the doses of BZDs that elicited other behavioral responses, including the ability to prevent PTZ-induced convulsions, a higher anti-proconflict index is predictive of an antipanic action for a special class of BZDs.

Idiopathic and Psychomotor Epilepsy

The importance of benzodiazepines (clonazepam and diazepam) in the treatment of idiopathic and psychomotor epilepsy is widely recognized. Indeed, benzodiazepines are "the drug of choice" and have resulted in a substantial reduction of mortality and morbidity and probably also in the frequent termination of serial seizures before a status epilepticus is established (J. Overweg, D. C. Binnie: Benzodiazepines in neurological disorders. In: Benzodiazepines: From Molecular Biology to Clinical Practice. E. Costa (ed.) Raven Press, New York, pp. 339–347, 1983).

The connection between GABAergic transmission convulsive disorders and the anticonvulsant activity of benzodiazepines is straight forward (See Haefely et al.: Neuropharmacology of Benzodiazepines: Synaptic Mechanisms and Neural Basis of Action In: The Benzodiazepines: From Molecular Biology to Clinical Practice, E. Costa (ed.) Raven Press, New York, pp. 21–66, 1983. Because of their molecular action on $GABA_A$ receptors, the most prominent effect of benzodiazepines in epilepsy occurs in structures that are notoriously proved to generate paroxysmal activity and that contain powerful GABAergic feedback circuits. Theoretically, benzodiazepines are the drugs of choice in limiting the tendency to explosive psychomotor seizures, triggered by abnormal discharges originating in the amygdala/hippocampal region Experimentally, diazepam and clonazepam are powerful agents to prevent the development of seizures that result from "kindling" (periodical electrical stimulation) of the amygdala in rats. However, the value of clonazepam and diazepam for chronic maintenance therapy is greatly reduced because of the rapid development of tolerance. Tolerance is known as the ability of a drug to lose effectiveness over time for various known and unknown biological reasons. Thus, the dose of a drug must be increased over time to achieve the same effect. Benzodiazepines are known to result in the development of tolerance which makes them less useful over time for their intended effect. The present invention has been accomplished with the above in mind. Therefore, the search for an effective antiepileptic benzodiazepine, which possesses low tolerance liability, low sedative action and which fails to cause ataxia has been for years an important goal in the treatment of epilepsy.

U.S. Pat. No. 4,280,957 generically discusses the compounds of the present invention, as well as thousands of other compounds, but contains no specific disclosure of the compounds of the present invention, or discussion that they are unexpectedly superior with respect to their antipanic effects, or that they are unexpectedly superior with respect to their low tolerance profile.

SUMMARY OF THE INVENTION

This invention relates to the pharmacologically active imidazo[1,5-a][1,4]benzodiazepine-3-carboxamide compounds. These compounds are partial agonists with high antipanic indices and are useful in treating anxiety disorders and epilepsy.

The chemical structure of these compounds may be depicted by the following formula

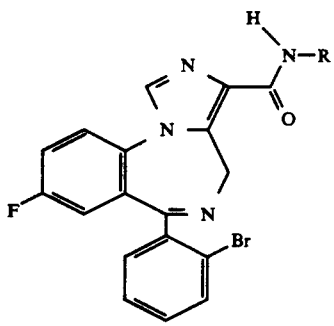

wherein R is hydrogen, CH$_3$CH$_2$—, (CH$_3$)$_2$CH—, CH$_3$CH$_2$CH$_2$—,

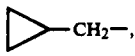

or CH$_2$=CHCH$_2$—, or a pharmaceutically acceptable salt thereof. A preferred embodiment of the invention is the compound of formula I wherein R is hydrogen or CH$_3$CH$_2$.

Figure 1:
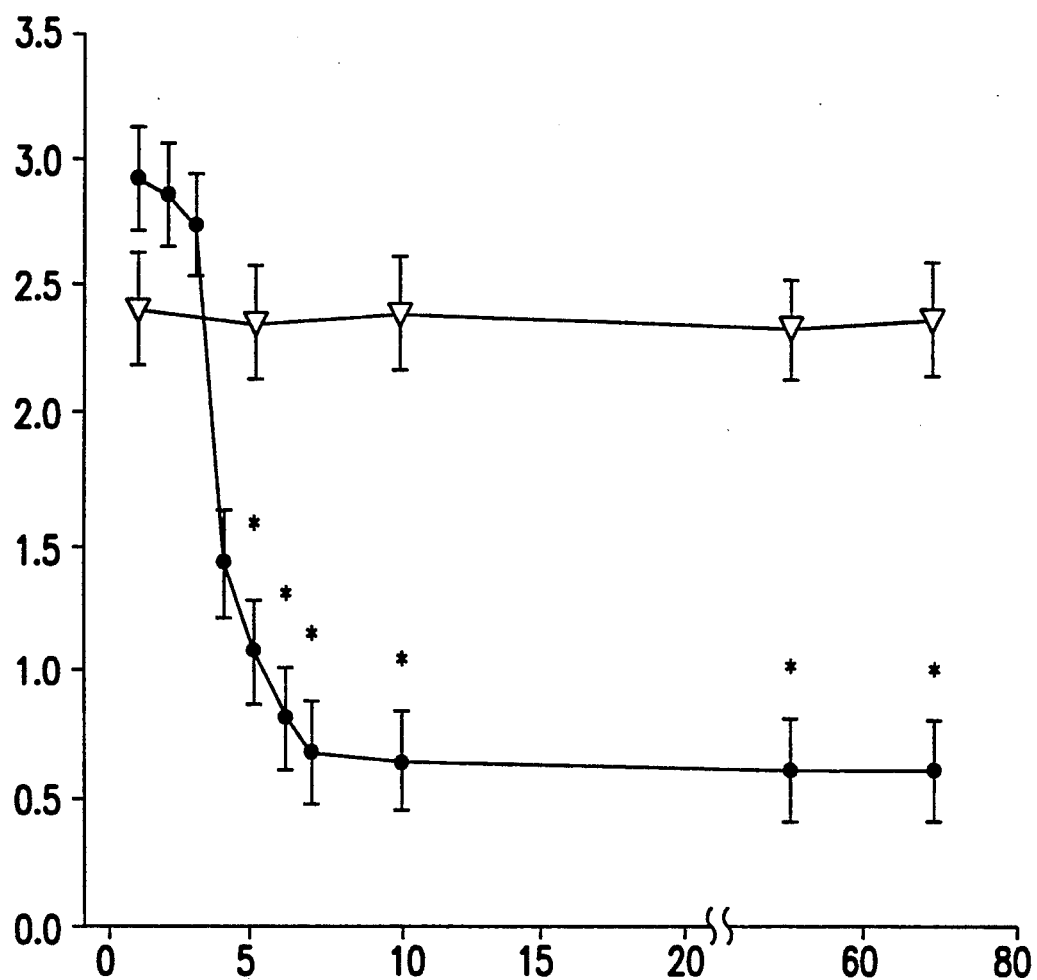
FIG. 1 shows the development of tolerance to the anticonvulsant effect of diazepam as compared with 6-(2-bromophenyl-8-fluoro-4H-imidazo[1,5-a][1,4]benzodiazepine-3-carboxamide during chronic administration.

- ●Diazepam dose 88 μmol/kg per os, three times a day; ▽6-(2-Bromophenyl-8-fluoro-4H-imidazo[1-,5a][1,4-benzodiazepine-3-carboxamide) dose 2.7 μmol/kg per os, three times a day.
- *<0.01 Dunnets test vs. control. The y axis represents the dose of bicucalline required (μmol/kg i.v.) to overcome the protective action of the tested compound The x axis represents the days of treatment.

DETAILED DESCRIPTION OF THE PREFERRED EMBODIMENTS

This invention relates to the pharmacologically active imidazo[1,5-a][1,4]benzodiazepine-3-carboxamide compounds. These compounds are partial agonists with high antipanic indices and are useful in treating panic disorders and epilepsy.

The chemical structure of these compounds may be depicted by the following formula

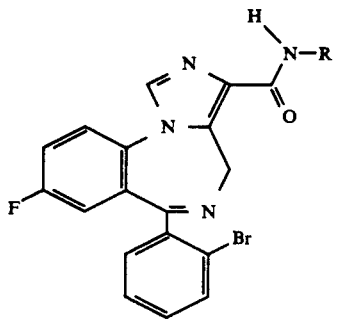

wherein R is hydrogen, CH$_3$CH$_2$—, CH$_2$=CHCH$_2$—, (CH$_3$)$_2$CH—, CH$_3$CH$_2$CH$_2$—or

or a pharmaceutically acceptable salt thereof. A preferred embodiment of the invention is the compound of formula I wherein R is hydrogen or CH$_3$CH$_2$—.

As used in this disclosure, the term "lower alkyl" comprehends both straight, cyclo and branched chain (C1–C4) hydrocarbon radicals such as methyl, ethyl, propyl, isopropyl, butyl and the like.

By the term "lower alkenyl" is meant straight or branched chain hydrocarbon radicals which contain an olefinic double bond and have from 3 to 5 carbon atoms.

The term "halogen" is used to include all four forms thereof, i.e. chlorine, bromine, fluorine and iodine.

The term "pharmaceutically acceptable salts", is used to include salts with both inorganic and organic pharmaceutically acceptable acids. Examples of such acids capable of forming salts with the compounds of formula I are hydrochloric acid, hydrobromic acid, nitric acid, sulfuric acid, phosphoric acid, methanesulfonic acid, paratoluenesulfonic acid and the like. Such salts can be formed quite readily by those skilled in the art, with the prior art and the nature of the compound to be placed in salt form, in view.

The compounds of formula I above can be prepared following a variety of synthetic routes of which the following schematic syntheses are exemplary.

The compounds of formula I can be synthesized as outlined in Scheme I. Unless otherwise indicated, R has the same meaning as set forth above. The reactions and reaction conditions similar to those of Scheme I are well known. See, e.g., Sternbach et al., J. Org. Chem., 27:3788–96 (1962) and U.S. Pat. No. 4,280,957.

The aminobenzophenone (formula II) was obtained by the reaction of 4-fluoroaniline with a 2-bromobenzoyl chloride, both of which are commercially available, in the presence of zinc chloride followed by acid hydrolysis.

The aminobenzophenone was converted to the haloacetyl derivative (formula III) by reaction with haloacetyl halide at room temperature in a suitable solvent.

The compound of formula III is converted into the diazepinone of formula IV according to known procedures, for example, by reacting the compound of formula III in a suitable solvent with liquid ammonia at reflux followed by a cyclization reaction through heating to reflux in a mixture of ethanol and acetic acid.

The lactam (formula IV) was activated by O-phophorylation with diethyl chlorophosphate in the presence of a strong base, such as alkali salts of t-butyl alcohol and condensed with the anion of ethyl isocyanoacetate also in the presence of a strong base, such as alkali salts of t-butyl alcohol, to form the imidazole ester (formula V). Acid hydrolysis of this ester led to the corresponding acid (R$^1$=H).

The amides of formula I were obtained by reaction of the acid (formula V) with phosphorus pentachloride in methylene chloride followed by treatment in situ with an excess of ammonia or of the appropriate amine.

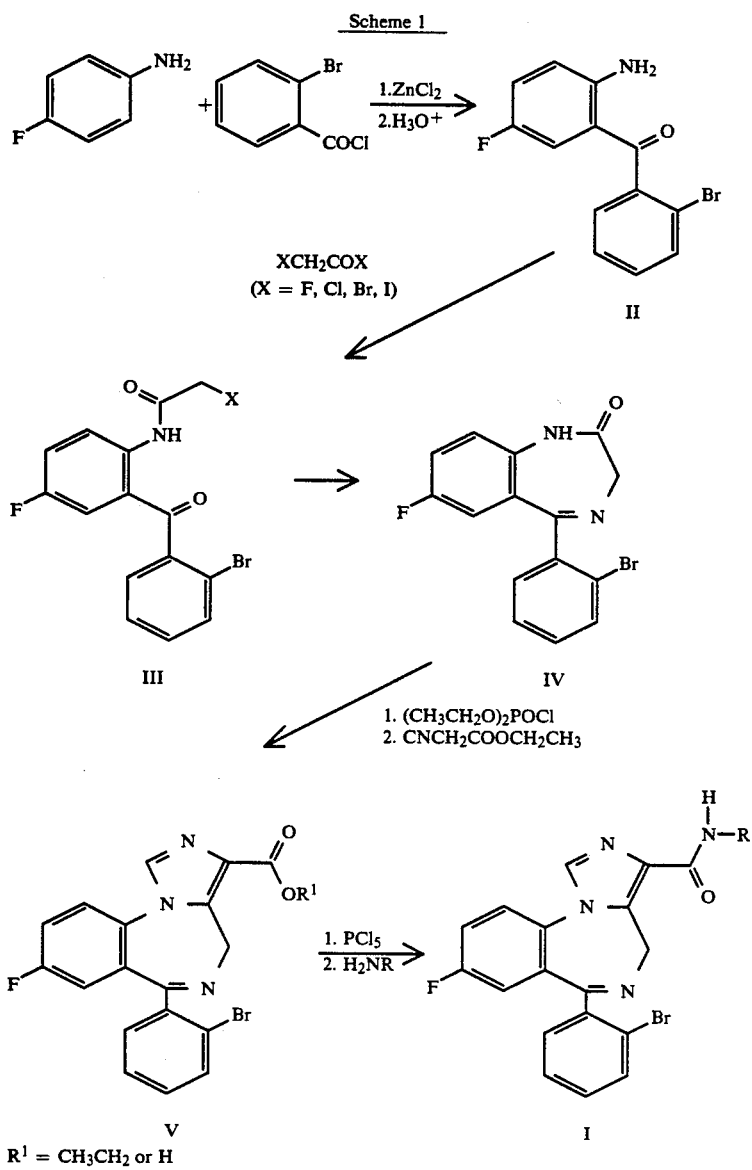

Scheme 1

An alternate method of synthesizing the lactam (formula IV) is depicted in Scheme II, below.

The aminobenzophenonimine (formula VI) was obtained by the reaction of 4-fluoroaniline with 2-bromobenzonitrile in the presence of anhydrous aluminum chloride and boron trichloride heated to reflux under nitrogen. This reaction can be carried out in any suitable solvent, for example, a mixture of toluene and 1,2-dichloroethane.

The aminobenzophenonimine was converted to the glycine methyl ester derivative (formula VII) by refluxing formula VI with glycine methyl ester hydrochloride in methanol.

The compound of formula VII was converted into the diazepinone of formula IV by refluxing formula VII with p-toluenesulfonic acid monohydrate in any suitable solvent such as toluene.

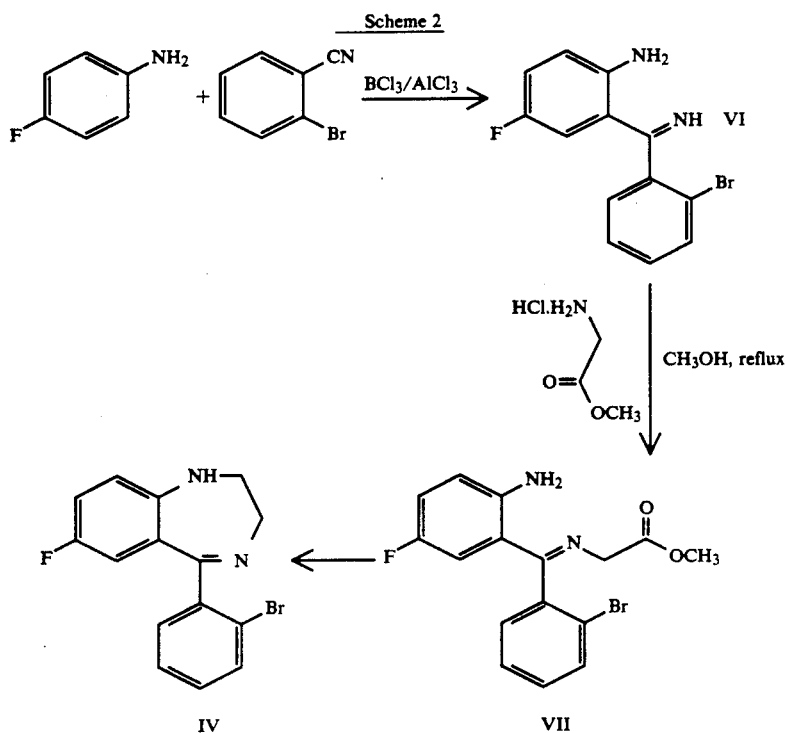

Scheme 2

Compounds of formula I and their pharmaceutically acceptable addition salts are useful as anti-anxiety agents and antiepileptic agents and can be administered orally, intravenously or intramuscularly. As contemplated by this invention, the compounds of formula I and their pharmaceutically acceptable acid addition salts can be embodied in pharmaceutical dosage formulations containing from about 0.1 mg to about 10 mg, most preferably about 0.2 mg to 2 mg with dosage adjusted to species and individual requirements.

The compounds of formula I and their pharmaceutically acceptable salts can be administered internally, for example, parenterally or enterally, in conventional pharmaceutical dosage forms, with pharmaceutically acceptable carriers. For example, they can be incorporated in conventional liquid or solid vehicles such as water, gelatin, starch, magnesium stearate, talc, vegetable oils and the like to provide tablets, elixirs, capsules, solutions, emulsions and the like according to acceptable pharmaceutical practices.

The following examples are illustrative but do not limit the present invention. All temperatures are stated in degrees Centigrade. Room temperature indicates a temperature between 20°–23° C.

EXAMPLE 1

(2-Amino-5-fluorophenyl)(2-bromophenyl)methanone

A mixture of 20 g (0.15 mol) of zinc chloride and 50 g (0.23 mol) of 2-bromobenzoyl chloride was heated to 110° C. 4-Fluoroaniline, 13 g (0.12 mol) Was added over a period of 2 minutes, raising the temperature of the mixture to 160° C. This mixture was then heated and stirred for 3 hours at 210°–220° C. After cooling to 140° C., 200 mL of hot 3N hydrochloric acid was added cautiously. The mixture was stirred and heated to reflux for 5 minutes and the aqueous phase was decanted from the residue. This procedure was repeated twice. The residue was dissolved in 200 mL acetic acid and treated with 100 mL of 3N hydrochloric acid and 10 mL of concentrated sulfuric acid to form a mixture.

This mixture was heated to reflux with stirring for 48 hours and then poured over ice and extracted with ether. The resulting ether extracts were washed with 2N sodium hydroxide solution, dried and evaporated. The residue was chromatographed over 300 g of silica gel using toluene. The fractions containing a yellow product were combined and evaporated to leave 12.6 g of yellow resin having the above formula. For analysis, a sample of the yellow resin was crystallized from ether/hexane and recrystallized from ethanol/hexane to give yellow crystals with m.p. 64°–66° C.

EXAMPLE 2

2-Bromo-N-[2-(2-bromobenzoyl)-4-fluorophenyl]acetamide

A solution of 2.95 g (10 mmol) of (2-amino-5-fluorophenyl)(2-bromophenyl)methanone in 50 mL of methylene chloride was layered with 50 mL of saturated sodium bicarbonate solution. Bromoacetyl bromide, 1.35 mL (15 mmol) was added to the organic layer and the mixture was stirred at room temperature for 15 minutes. The organic layer was separated, dried and evaporated. The residue was crystallized from ether/hexane to yield 3.85 g of product having the above formula with m.p. 110°–114° C. For analysis, a sample of product was recrystallized from ether/hexane to leave colorless crystals with m.p. 113°–115° C.

EXAMPLE 3

5-(2-Bromophenyl)-7-fluoro-1,3-dihydro-1,4-benzodiazepin-2(2H)-one

A solution of 15 g (36 mmol) of 2-bromo-N-[(2-bromobenzyol)-4-fluorophenyl]acetamide in 150 mL of me chloride was added to 250 mL of liquid ammonia. After stirring and refluxing for 18 hours, the ammonia had evaporated. The residue was washed with water and the methylene chloride layer was dried and evaporated. The residue was heated to reflux for 2 hours in 200 mL of ethanol containing 7 mL of acetic acid. The solvent was evaporated and the residue was crystallized from methylene chloride/ethanol to yield 10 g of product having the above formula. For analysis, a sample of the product was recrystallized from tetrahydrofuran/ethanol and had a m.p. 194°-196° C.

EXAMPLE 4

(2-Amino-5-fluorophenyl)(2-bromophenyl)methanimine

To a solution of 668.1 g (6.012 moles) of 4-fluoroainiline in a mixture of 7.2 L of toluene and 2.7 L of 1,2-dichloroethane, was added 477.7 g (3.583 moles) of anhydrous aluminum chloride under nitrogen. The mixture was stirred for 15 minutes and 3.0 L (3.0 moles) of 1.0 M solution of boron trichloride in xylene was added over a period of 15 minutes. A solution of 545.1 g (2.995 moles) of 2-bromobenzonitrile in 1.0 L of toluene was then added in one portion. The mixture was heated to reflux under nitrogen for 20 hours, then cooled and poured over crushed ice, 6.8 L of concentrated ammonium hydroxide, and 8.0 L of methylene chloride. A solution of 6.8 L of 6.0 N aqueous potassium hydroxide was slowly added with vigorous stirring. The organic layer was separated and the aqueous layer was extracted with 4.0 L of methylene chloride. The combined organic extracts were washed twice with an equal volume of deionized water, dried over $Na_2SO_4$, filtered, and concentrated under vacuum to a volume of 5 L. The concentrated mixture was then combined with the product of a second batch obtained in a similar manner as above and the combined mixtures were concentrated under vacuum to give 1,515 g of residue. The residue was dissolved in methylene chloride and chromatographed over 4.0 kg of silica gel using 9:1 hexane:ethyl acetate. The fractions containing the product were combined, concentrated, and dried under high vacuum to give 1,313.5 g of (2-amino-5- fluorophenyl)(2-bromophenyl)methanimine.

EXAMPLE 5

(Z)-N-[{2-Amino-5-fluorophenyl)(2-bromophenyl)methylene]glycine methyl ester)

A solution of 139.5 g (0.446 moles) of (2-amino-5-fluorophenyl)(2-bromophenyl)methanimine, 69.9 g (0.557 moles) of glycine methyl ester hydrochloride and 1.68 L of methanol was stirred at reflux for 5 hours under nitrogen. The solvent was then removed by evaporation under vacuum and the yellow, residual solid was partitioned between 1.4 L of methylene chloride and 1.4 L of saturated $NaHCO_3$ solution. The organic layer was separated and the aqueous layer was extracted with 0.5 L of methylene chloride. The combined organic extracts were dried with $Na_2SO_4$, filtered, and concentrated under vacuum. The residue was redissolved in 0.5L of methylene chloride and concentrated to a dark yellow semi-solid (156.6 g). This solid was recrystallized from 400 mL of 1:3 EtOAc/Hexane to give 72.8 of (Z)-N-[(2-Amino-5-fluorophenyl)(2-bromophenyl)methylene]glycine methyl ester).

EXAMPLE 6

5-(2-Bromophenyl)-7-fluoro-1,3-dihydro-1,4-benzodiazepine-2(2H)-one

A solution of 72.7 g (0.199 moles) of (Z)-N-[(2-amino-5-fluorophenyl)(2-bromophenyl)methylene]glycine methyl ester), 1450 mL of toluene, and 42.8 g (0.225 moles) of p-toluenesulfonic acid monohydrate was heated to reflux for 3 hours under nitrogen After cooling, the product crystallized out of the reaction mixture The resultant suspension was filtered and the collected solid was washed twice with 100 mL of toluene, followed by two washes with 100 mL of hexane. The solid was partitioned between 1.0 L of methylene chloride and 1.0 L of saturated $NaHCO_3$ solution. The organic layer was separated and the aqueous layer was extracted with 250 mL of methylene chloride. The combined organic layers were washed twice with 250 mL of 1:1 mixture brine/water, dried with $Na_2SO_4$, filtered, and concentrated under vacuum. The residue was redissolved in 800 mL of methylene chloride and concentrated to give 55.5 g of 5-(2-bromophenyl)-7-fluoro-1,3-dihydro-1,4-benzodiazepine-2(2H)-one as a light yellow solid.

EXAMPLE 7

6-(2-Bromophenyl)-8-fluoro-4H-imidazo[1,5-a][1,4]benzodiazepine-3-carboxylic acid ethyl A solution of 10 g (0.03 mol) of 5-(2-bromophenyl)-7-fluoro-1,3-dihydro-1,4-benzodiazepine-2of tetrahydrofuran was cooled to −20° C. Potassium tertiary butoxide, 3.7 g (0.0327 mol), was added and the mixture was stirred under nitrogen for 5 minutes. Diethyl chlorophosphate, 5.25 mL, was then added and stirring was continued without cooling until the temperature reached 10° C. The mixture was cooled again to −20° C. and treated with 4.2 mL of ethyl isocyanoacetate and then with 4.05 g (0.0358 mol) of potassium tert-butoxide. The mixture was stirred without cooling for 1.5 hours.

The mixture was acidified by addition of 10 mL of acetic acid and partitioned between toluene and saturated aqueous sodium bicarbonate solution The organic layer was dried and evaporated and the residue was crystallized from ethyl acetate/ether/hexane to yield 8.3 g of product having the above formula with m.p. 209°-210° C. A different crystalline modification with m.p. 196-198° C. was also observed upon crystallization from methylene chloride/ethyl acetate.

EXAMPLE 8

6-(2-Bromophenyl)-8-fluoro-4H-imidazo[1,5-a][1,4]benzodiazepine-3-carboxylic acid A suspension of 8 g (18.65 mmol) of 6-(2-bromophenyl)-8-fluoro-4H-imidazo[1,5-a][1,4]benzo-diazepine-3-carboxylic acid ethyl ester in 200 mL of 6N-hydrochloric acid was heated on a steam bath for 18 hours. The solution was evaporated under reduced pressure and the residue was dissolved in 50 mL of water with heating. Sodium acetate, 8 g, was added and heating on the steam bath was continued while the product crystallized out of solution After cooling on ice, the product was filtered off, washed with water and sucked dry. This crude product was dissolved in tetrahydro-furan/methylene chloride/ethanol. The solution was filtered and the filtrate was partially evaporated after addition of 5 mL of water and 1 mL of acetic acid. The precipitated crystals having the above formula were collected and dried at 100° C. under vacuum to leave 6 g of product with m.p. 280°-285° C. A second crop of 0.9 g was recovered from the original filtrate and from the mother liquor. For analysis, a sample of the product was recrystallized from tetrahydro-furan-/ethanol and had the same m.p.

EXAMPLE 9

6-(2-Bromophenyl)-8-fluoro-4H-imidazo[1,5-a][1,4]benzodiazepine-3-carboxamide

A mixture of 3 g (7.5 mmol) of 6-(2-bromophenyl)-8-fluoro-4H-imidazo[1,5-a][1,4]benzodiazepine-3-carboxylic acid, 300 mL of methylene chloride and 2.25 g (10.8 mmol) of phosphorus pentachloride was stirred at room temperature for 2 hours. Ammonia gas was then introduced until the mixture was basic. After layering with 20 mL of concentrated aqueous ammonia, the mixture was stirred for 15 minutes. The methylene chloride was washed with water, dried and evaporated. The residue was crystallized from ethanol/water to yield 2.4 g of product having the above formula. A second crop of 0.4 g was obtained from the mother liquor for a total yield of 2.8 g. For analysis, a sample of the product was recrystallized from methylene chloride/ethanol and had m.p. 298°-299° C.

EXAMPLE 10

6-(2-Bromophenyl)-N-ethyl-8-fluoro-4H-imidazo[1,5-a][1,4]-benzodiazepine-3-carboxamide A mixture of 0.4 g (1 mmol) of 6-(2-bromophenyl)-8-fluoro-4H-imidazo[1,5-a][1,4]benzodiazepine-3-carboxylic acid, 50 mL of methylene chloride and 0.3 g (1.44 mmol) of phosphorus pentachloride was stirred at room temperature for 2.5 hours. Ethylamine was introduced until the reaction mixture was basic. It was layered with 10% aqueous sodium carbonate solution and the two phases were stirred for 15 minutes The organic layer was separated, dried and evaporated. The residue was crystallized from ethyl acetate/hexane to yield 0.37 g of product having the above formula. For analysis it was recrystallized from ethanol to leave colorless crystals with m.p. 218°-220° C.

EXAMPLE 11

In a similar fashion to Example lo, the following compounds were prepared, except in place of ethylamine, the corresponding alkylamine was added in excess:

(a) 6-(2-Bromophenyl)-8-fluoro-N-propyl-4H-imidazo[1,5-a]1,4]benzodiazepine-3-carboxamide, m.p. 184°-186° C., crystallized from methylene chloride/ethyl acetate/hexane.
(b) 6-(2-Bromophenyl)-8-fluoro-N-(1-methylethyl)-4-H-imidazo[1,5-a][1,4]benzodiazepine-3-carboxamide, m.p 228°-230° C., crystallized from methylene chloride/ethyl acetate/hexane.
(c) 6-(2-Bromophenyl)-8-fluoro-N-(2-propenyl)-4H-imidazo[1,5-a][1,4]benzodiazepine-3-carboxamide, m.p. 149°-151° C., crystallized from ethyl acetate/hexane.
(d) 6-(2-Bromophenyl)-N-[(cyclopropyl)methyl]-8-fluoro-4H-imidazo[1,5-a][1,4]benzodiazepine-3-carboxamide, m.p. 188°-190° C., crystallized from ethyl acetate.

EXAMPLE 12

Wet Granulation Formulation

| Ingredients | mg/tablet | | |
|---|---|---|---|
| 1. 6-(2-Bromophenyl)-8-fluoro-4H-imidazo[1,5-a] [1,4] benzodiazepine-3-carboxamide | 0.1 | 0.5 | 5.0 |
| 2. Lactose Anhydrous DTG | 106.9 | 106.5 | 102.0 |
| 3. Avicel PH 102 | 15.0 | 15.0 | 15.0 |
| 4. Modified Starch | 7.0 | 7.0 | 7.0 |
| 5. Magnesium Stearate | 1.0 | 1.0 | 1.0 |
| TOTAL | 130.0 | 130.0 | 130.0 |

Manufacturing Procedure

1) Dissolve 6-(2-Bromophenyl)-8-fluoro-4H-imidazo[1,5-a][1,4]benzodiazepine-3-carboxamide in a suitable solvent such as alcohol.
2) Spread this solution over the lactose and dry.
3) To this dried power add the Avicel and modified starch and mix for 10 minutes.
4) To this mix add magnesium stearate and mix for 3 minutes and compress.

EXAMPLE 13

Capsule Formulation

| Ingredients | mg/capsule | | |
|---|---|---|---|
| 1. 6-(2-Bromophenyl)-8-fluoro-4H-imidazo[1,5-a] [1,4] benzodiazepine-3-carboxamide | 0.1 | 0.5 | 5.0 |
| 2. Lactose Anhydrous DTG | 168.9 | 168.5 | 159.0 |
| 3. Avicel PH 102 | 20.0 | 20.0 | 25.0 |
| 4. Modified Starch | 10.0 | 10.0 | 10.0 |
| 5. Magnesium Stearate | 1.0 | 1.0 | 1.0 |
| TOTAL | 200.0 | 200.0 | 200.0 |

Manufacturing Procedure

1) Mix 6-(2-Bromophenyl)-8-fluoro-4H-imidazo[1,5-a][1,4]-benzodiazepine-3-carboxamide, lactose hydrous and corn starch in a suitable mixer for 30 minutes.
2) To this mixture add talc and magnesium stearate and mix for 3 minutes.
3) Fill into suitable capsule.

EXAMPLE 14

Inhalation Aerosol Formulation (Suspension)

| Item | Ingredients | % w/w |
|---|---|---|
| 1. | 6-(2-Bromophenyl)-8-fluoro-4H-imidazo[1,5-a] [1,4] benzodiazepine-3-carboxamide | 1.0 |
| 2. | Sorbitan Trioleate | 0.5 |
| 3. | Freon 12 | 64.0 |
| 4. | Freon 11 | 18.5 |
| 5. | Freon 114 | 16.0 |
| TOTAL | | 100% |

Manufacturing Procedure

1) Mix 6-(2-Bromophenyl)-8-fluoro-4H-imidazo[1,5-a]-[1,4]benzodiazepine-3-carboxamide and sorbitan trioleate into Freon 11 and homogenize.

2) Fill this concentrate suspension into a suitable can and place in valve and crimp to seal container.
3) Pressure-fill a 80:20 mixture of Freon 12 and Freon 114.

NOTE: A suitable valve may be used to deliver 25 to 100 microliters in volume.

EXAMPLE 15

Capsule Formulation

| | Ingredients | mg/capsule | | |
|---|---|---|---|---|
| 1. | 6-(2-Bromophenyl)-N-ethyl-8-fluoro-4H-imidazo[1,5-a][1,4]benzodiazepine-3-carboxamide | 0.1 | 0.5 | 5.0 |
| 2. | Lactose Hydrous | 168.9 | 168.5 | 159.0 |
| 3. | Corn Starch | 20.0 | 20.0 | 25.0 |
| 4. | Talc | 10.0 | 10.0 | 10.0 |
| 5. | Magnesium Stearate | 1.0 | 1.0 | 1.0 |
| | TOTAL | 200.0 | 200.0 | 200.0 |

Manufacturing Procedure

1) Mix 6-(2-Bromophenyl)-N-ethyl-8-fluoro-4H-imidazo[1,5-a][1,4]benzodiazepine-3-carboxamide, lactose hydrous, corn starch in a suitable mixer for 30 minutes.
2) To this mixture add talc, magnesium stearate and mix for 3 minutes.
3) Fill into suitable capsule.

EXAMPLE 16

Wet Granulation Formulation

| | Ingredients | mg/tablet | | |
|---|---|---|---|---|
| 1. | 6-(2-Bromophenyl)-N-ethyl-8-fluoro-4H-imidazo[1,5-a][1,4]benzodiazepine-3-carboxamide | 0.1 | 0.5 | 5.0 |
| 2. | Lactose Anhydrous DTG | 106.9 | 106.5 | 102.0 |
| 3. | Avicel PH 102 | 15.0 | 15.0 | 15.0 |
| 4. | Modified Starch | 7.0 | 7.0 | 7.0 |
| 5. | Magnesium Stearate | 1.0 | 1.0 | 1.0 |
| | TOTAL | 130.0 | 130.0 | 130.0 |

Manufacturing Procedure

1) Dissolve 6-(2-Bromophenyl)-N-ethyl-8-fluoro-4H-imidazo[1,5-a][1,4]benzodiazepine-3-carboxamide in a suitable solvent such as alcohol.
2) Spread this solution over lactose anhydrous DTG, dry.
3) To this combination add Avicel PH 102, modified starch and mix for 10 minutes.
4) To this mixture add magnesium stearate and mix for 3 minutes and compress.

EXAMPLE 17

Inhalation Aerosol Formulation (Suspension)

| Item | Ingredients | % w/w |
|---|---|---|
| 1. | 6-(2-Bromophenyl)-N-ethyl-8-fluoro-4H-imidazo[1,5-a] [1,4] benzodiazepine-3-carboxamide | 1.0 |
| 2. | Sorbitan Trioleate | 0.5 |
| 3. | Freon 12 | 64.0 |
| 4. | Freon 11 | 18.5 |
| 5. | Freon 114 | 16.0 |

-continued

| Item | Ingredients | % w/w |
|---|---|---|
| | TOTAL | 100% |

Manufacturing Procedure

1) Mix 6-(2-Bromophenyl)-N-ethyl-8-fluoro-4H-imidazo[1,5-a][1,4]benzodiazepine-3-carboxamide and sorbitan trioleate into Freon 11 and homogenize.
2) Fill this concentrate suspension into a suitable can and place in valve and crimp to seal container.
3) Pressure-fill a 80:20 mixture of Freon 12 and Freon 114.

NOTE: A suitable valve may be used to deliver 25 to 100 microliters in volume.

EXAMPLE 18

Capsule Formulation

| | Ingredients | mg/capsule | | |
|---|---|---|---|---|
| 1. | 6-(2-Bromophenyl)-8-fluoro-N-(2-propenyl)-4H-imidazo [1,5-a] [1,4]benzodiazepine-3-carboxamide | 0.1 | 0.5 | 0.5 |
| 2. | Lactose Anhydrous DTG | 168.9 | 168.5 | 159.0 |
| 3. | Avicel PH | 20.0 | 20.0 | 25.0 |
| 4. | Modified Starch | 10.0 | 10.0 | 10.0 |
| 5. | Magnesium Stearate | 1.0 | 1.0 | 1.0 |
| | TOTAL | 200.0 | 200.0 | 200.0 |

Manufacturing Procedure

1) Mix 6-(2-Bromophenyl)-8-fluoro-N-(2-propenyl)-4H-imidazo[1,5-a][1,4]benzodiazepine-3-carboxamide, lactose anhydrous DTG, Avicel PH 102 in a suitable mixer for 30 minutes.
2) To this mixture add modified starch, magnesium stearate and mix for 3 minutes.
3) Fill into suitable capsule.

EXAMPLE 19

Wet Granulation Formulation

| | Ingredients | mg/tablet | | |
|---|---|---|---|---|
| 1. | 6-(2-Bromophenyl)-8-fluoro-N-(2-propenyl)-4H-imidazo [1,5-a] [1,4] benzodiazepine-3-carboxamide | 0.1 | 0.5 | 5.0 |
| 2. | Lactose Anhydrous DTG | 106.9 | 106.5 | 102.0 |
| 3. | Avicel PH 102 | 15.0 | 15.0 | 15.0 |
| 4. | Modified Starch | 7.0 | 7.0 | 7.0 |
| 5. | Magnesium Stearate | 1.0 | 1.0 | 1.0 |
| | TOTAL | 130.0 | 130.0 | 130.0 |

Manufacturing Procedure

1) Dissolve 6-(2-Bromophenyl)-8-fluoro-N-(2-propenyl)-4H-imidazo[1,5-a][1,4]benzodiazepine-3-carboxamide in a suitable solvent such as alcohol.
2) Spread this solution over lactose anhydrous DTG, dry.
3) To this combination, add Avicel PH 102, modified starch and mix for 10 minutes.
4) To this mixture add magnesium stearate and mix for 3 minutes and compress.

EXAMPLE 20

Inhalation Aerosol Formulation (Suspension)

| Item | Ingredients | % w/w |
|---|---|---|
| 1. | 6-(2-Bromophenyl)-8-fluoro-N-(2-propenyl)-4H-imidazo[1,5-a][1,4]benzodiazepine-3-carboxamide | 1.0 |
| 2. | Sorbitan Trioleate | 0.5 |
| 3. | Freon 12 | 64.0 |
| 4. | Freon 11 | 18.5 |
| 5. | Freon 114 | 16.0 |
| TOTAL | | 100% |

Manufacturing Procedure

1) Mix 6-(2-Bromophenyl)-8-fluoro-N-(2-propenyl)-4H-imidazo[1,5-a][1,4]benzodiazepine-3-carboxamide and sorbitan trioleate into Freon 11 and homogenize.
2) Fill this concentrate suspension into a suitable can and place in valve and crimp to seal container.
3) Pressure-fill a 80:20 mixture of Freon 12 and Freon 11.

NOTE: A suitable valve may be used to deliver 25 to 100 microliters in volume.

EXAMPLE 21

To examine the anti-panic activity of the compounds of the present invention, the experiments described below were performed. These experiments measure the anticonflict and antiproconflict effects of the inventive compounds. These values are used to calculate an anti-proconflict index, which is predictive of anti-panic activity. The experiments are described in detail in Guisti et al. (1991), *J. Pharm. Exp. Ther.* Vol. 257 (3), pp. 1062–1068.

(a) punished drinking behavior

For these experiments the punishment behavioral paradigm developed by Vogel et al., Psychopharmalogy 21:1–7 (1971) and modified by Corda et al., P.N.A.S. 80:2070–76 (1983) was used. Animals were deprived of water for 72 hours before the experiment. Each rat was allowed to become familiar with a habituation chamber (a chamber identical to the testing chamber but without water) for 5 minutes immediately before the test in order to avoid exploration-induced delay in drinking. After this period, the rat was transferred to the testing chamber (28×20×20 cm with a stainless steel grid floor). Water was provided with a stainless steel drinking tube (See Corda et al., supra). Each rat was allowed to complete a 10 second licking period before the start of a 3 minute test period. The number of licking periods (each period equal to 3 seconds of cumulative drinking) was recorded in unpunished rats and in rats punished with an electric shock delivered through the drinking tube after each drinking period. Programming for the test session was controlled by a solid-state modular programming apparatus. Rats that failed to start drinking within 5 minutes of being placed in the test chamber were excluded from the experiment.

The two experimental paradigms used were termed *conflict* and *proconflict*. In the conflict paradigm, punishment was set to an intensity of 0.8 mA of 1 second duration. In the proconflict paradigm, punishment was delivered with a shock of 0.35 mA for 1 second, but in addition, rats were treated with PTZ (145 mmol/kg i.p.) 15 minutes before the test. The terms anticonflict and anti-proconflict are used to denote the protective action of a compound against the conflict or proconflict paradigms, respectively.

The compounds were either injected intravenously in a volume of 2.0 μl/kg, or intramuscularly in a volume of 3.0 μl/kg, and their doses are expressed in μmol/kg. The compounds were administered 15 minutes before the test.

(b) Calculation of the Anti-proconflict Index

The anticonflict and anti-proconflict effects of the compounds were calculated as a percentage protection as follows:

$$protection = (A-K)/(B-K) \times 100\%$$

where

A = average number of licking periods in a group of drug-treated rats receiving punishment, B = average number of licking periods in a group of drug-treated rats not receiving punishment, and K = average number of licking periods in a group of saline-treated rats receiving punishment.

For the doses of the compounds tested, the average number of licking periods for drug-treated rats in the absence of punishment (B) does not differ from the average number of licking periods in untreated unpunished rats. The relative potency of the compounds ($ED_{50}$ = dose of compound that gives 50% protection) in the conflict and proconflict test was derived from the percentage protection data by probit analysis according to Finney, Probit Analysis, Cambridge University Press (3rd Ed. 1971). After the parallelism between the anticonflict and anti-proconflict effects of a compound was verified, the same statistical analysis (Finney, suora) was used to calculate the anti-proconflict index and its fiducial limits as the difference between the logarithms of the $ED_{50}$ values for the anticonflict and proconflict action of each compound. For all these parameters the fiducial limits were referred to P=0.01. The anti-proconflict index was not calculated for compounds that failed to give 50% protection. In this case, the average number of licking periods and the standard error (SE) are reported, and the statistical difference from control group was evaluated with the Dunnett test (Dunnett, Biometrics 20:482–91, 1964). Table 1 compares the anticonflict and anti-proconflict effects obtained in the experiments described in Example 21 of compounds of formula I with that of Bretazenil (an antipanic drug as described in, Haefely, W. E., TIPS 11:452–456 (1991); and Katschnig, H., et al. In Biologische Psychiatrie, Ed. by B. Saletu pp. 167–169, Georg Thieme, N.Y., 1989; diazepam (an anxiolytic drug) and 8-chloro-6-(2-chlorophenyl)-4H-imidazo-[1,5-a][1,4]benzodiazepine-3-carboxamide, a structurally similar compound disclosed in U.S. Pat. No. 4,280,957. Although these compounds have different potencies, all elicted maximal anticonflict action at doses, that per se, fail to modify the drinking behavior. The table gives the $ED_{50}$ values and the fiducial limits for the different compounds in the conflict and proconflict test. Thus, diazepam has similar potency in the conflict and proconflict test, whereas all the tested compounds are more potent in the proconflict than in the conflict paradigm. Therefore, the ratio of the $ED_{50}$ values for anticonflict/antiproconflict action for each drug represents an anti-proconflict index. This index (a predictive value of antipanic activity) varies from the value of 1 for diazepam to 12 for the antipanic drug Bretazenil. It is noted that 6-(2-bromophenyl)-8-fluoro-4H-imidazo[1,5-a][1,4]benzodiazepine-3-carboxamide, 6-(2-bromophenyl)-N-ethyl-8-fluoro-4H-imidazo[1,5-a][1,4]benzodiazepine-3-carboxamide, and 6-(2-bromophenyl)-8-fluoro-N-(2-propenyl)-4H-imidazo[1,5-a]-[1,4]benzodiazepine-3-carboxamide have a antiproconflict index larger than that of Bretazenil, a known antipanic agent and unexpectedly much higher than the structurally similar 8-chloro-6-(2-chlorophenyl)-4H-imidazo-[1,5-a][1,4]benzodiazepine-3-carboxamide compound of the prior art. Accordingly, these compounds have significant anti-panic activity.

The compounds of the present invention act at a number of $GABA_A$ receptor subtypes with partial intrinsic efficacy and exhibit potent anti-proconflict action. In the context of the present invention, that is, the compounds of the present invention have an anti-proconflict index larger than 10. Therefore, it can be predicted that these compounds represent a new class of useful therapeutic agents for the treatment of panic disorders. However, an anti-proconflict index lower than 10 can also have the desired pharmacological action when the compounds have a slow elimination rate from the body. Compounds 11(a), 11(b) and 11(d), although having anti-proconflict indexes <10, are better than diazepam (compare anti-proconflict indices), and when given equipotent doses to Bretazenil, have a longer duration of action of from 3–6 hours, which is unexpectedly better than Bretazenil, which has a duration of action of only from 15–45 minutes.

TABLE 1

ANTI-PROCONFLICT INDEX FOR VARIOUS IMIDAZO-BENZODIAZEPINES
(Values in brackets include fiducial limits (P = 0.05)

| Compound | ED50 (μmol/kg, i.v.) | | |
|---|---|---|---|
| | Anticonflict Effect | Anti-Proconflict Effect | Anti-Proconflict Index |
| Reference Compound | | | |
| Bretazenil | 2.4 (1.7–3.1) | 0.20 (0.12–0.43) | 12 (5.2–20) |
| Inventive Compound | | | |
| (Example 9) 6-(2-Bromophenyl)-8-fluoro-4H-imidazo[1,5-a][1,4]benzodiazepine-3-carboxamide | 2.9 (1.0–5.9) | 0.061 (0.024–0.22) | 48 (16–58) |
| (Example 10) 6-(2-Bromophenyl)-N-ethyl-8-fluoro-4H-imadazo[1,5-a][1,4]benzodiazepine-3-carboxamide | 2.8 (1.2–6.3) | 0.079 (0.051–0.13) | 35 (12–92) |
| (Example 11(c)) 6-(2-Bromophenyl)-8-fluoro-N-(2-propenyl)-4H-imadazo[1,5-a][1,4]benzodiazepine-3-carboxamide | 3.6 (2.5–4.4) | 0.18 (0.13–2.80) | 20 (12–32) |
| (Example 11(b)) 6-(2-Bromophenyl)-8-fluoro-N-(1-methylethyl)-4H-imidazo[1,5-a][1,4]benzodiazepine-3-carboxamide | 1.72 (0.45–6.4) | 0.52 (0.090–2.90) | 3.3 (0.34–32) |
| (Example 11(a)) 6-(2-Bromophenyl)-8-fluoro-N-propyl-4H-imidazo[1,5-a][1,4]benzodiazepine-3-carboxamide | 2.74 (1.6–4.8) | 0.44 (0.12–1.5) | 6.3 (1.4–28) |
| (Example 11(d)) 6-(2-Bromophenyl)-N-[(cyclo-propyl)methyl]-8-fluoro-4H-imidazo[1,5-a][1,4]benzodiazepine-3-carboxamide | 3.3 (2.1–5.4) | 0.43 (0.10–1.8) | 7.7 (1.7–35) |

TABLE 1-continued

ANTI-PROCONFLICT INDEX FOR VARIOUS IMIDAZO-BENZODIAZEPINES
(Values in brackets include fiducial limits (P = 0.05)

| Compound | ED50 (μmol/kg, i.v.) | | |
|---|---|---|---|
| | Anticonflict Effect | Anti-Proconflict Effect | Anti-Proconflict Index |
| Reference Compound | | | |
| 6-(2-chlorophenyl)-8-chloro-4H-imidazo[1,5-a][1,4]benzodiazepine-3-carboxamide | 2.0 (1.5–5.0) | 0.45 (0.15–2.0) | 5.0 (1.5–10) |
| Reference Compound | | | |
| Diazepam | 2.0 (1.4–2.8) | 1.9 (1.5–2.5) | 1 (0.65–1.6) |

EXAMPLE 22

The present experiment shows the usefulness of the inventive compounds in the treatment of psychomotor epilepsy and their estimated low level of tolerance liability and longer duration of action. The antiepileptic potency, duration of action and tolerance liability of the inventive compounds is compared to that of diazepam, which could be considered the drug of choice for the treatment of epilepsy, if undesirable tolerance liability was not associated with this compound.

a) Chemical Kindling with Pentylenetetrazole (PTZ)

Kindled seizures were induced in rats by i.p. injection of 30 mg/kg of PTZ every 2nd day for 9 weeks. The day of the experiments, the rats were administered the inventive compounds or diazepam per os, 30 min. before the i.p. injection of PTZ and observed for 30 min. for the occurrence of seizures. Table 2 compares the potency of 6-(2-bromophenyl)-8-fluoro-4H-imidazo[1,5-a][1,4]benzodiazepine-3-carboxamide to that of diazepam in the kindling seizure test elicited by repeated administration of PTZ. As can be observed, the inventive compound was approximately 20 fold more potent that diazepam in this test. The inventive compound of Example 10 is 12-fold more potent than diazepam, while compounds of Examples 11(b), 11(a) and 11(d) are 2.5, 2.2 and 2-fold more potent than diazepam, respectively.

b) Development of Tolerance to the Anticonvulsant Effect of Diazepam and Inventive Compounds Equieffective oral doses of diazepam and 6-(2-bromophenyl)-8-fluoro-4H-imidazo[1,5-a][1,4]benzodiazepine-3-carboxamide against seizures induced with bicuculline infusions were used for these experiments. The bicuculline seizure test (see Massotti et al., J. Pharmacol. Exp. Ther. 256: 1154–1156, 1991) consists in infusing a bicuculline solution (0.27 μmol/kg) into the rat tail vein at a constant rate (0.46 ml/min) and records the first sign of myoclonic jerk and the full myoclonic convulsion. The dose of bicuculline required to elicit these responses was taken as an index of the efficacy of diazepam and inventive compounds against seizures induced by a decrease of GABAergic tone (Massotti et al., J. Pharmacol. Exp. Ther. 256: 1154–1160, 1990). Once equipotent oral doses of the inventive compounds and diazepam (88 μmol/kg) were established, rats were administered with these doses 3 times daily up to 70 days. Possible development of tolerance to the antagonism of bicuculline convulsion was tested on various days after the beginning of the protracted treatment with the inventive compounds. As shown in FIG. 1, tolerance to the anticonvulsant action of diazepam developed after a few days of treatment which is virtually complete after 5 to 7 days. In contrast, 6-(2-bromophenyl)-8-fluoro-4H-imidazo[1,5-a][1,4]benzodiazepine-3-carboxamide maintained its anticonvulsant effect unabated without tolerance even after 70 days of continuous treatment. Similarly, the other inventive compounds fail to develop anticonvulsant tolerance up to 70 days of treatment. It is important to note that the inventive compounds have a much longer duration of action (3–6 hours) than equipotent doses of the Bretazenil (15–45 minutes). Table 3 indicates that the imidazobenzo-diazepines are devoid of toxicity in mice for doses as high as 4 g/kg. The results indicate that the compounds of the present invention act as potent, efficacious and specific anticonvulsant agents. Moreover, unlike the classical benzodiazepines (e.g., diazepam) these compounds fail to induce tolerance.

Therefore, it can be predicted that compounds of the present invention represent a new, potent and safe class of therapeutic agents for the treatment of psychomotor epilepsy.

TABLE 2

Effects of Diazepam and 6-(2-Bromophenyl)-8-fluoro-4H-imidazo[1,5-a] [1,4] benzodiazepine-3-carboxamide on chemical kindling with PTZ

| ED$_{50}$ vs kindled seizures | | n |
| --- | --- | --- |
| Diazepam | 5.7 (2.9–11.2) | 25 |
| 6-(2-bromophenyl)-8-fluoro-4H-imidazo [1,5-a] [1,4] benzodiazepine-3-carboxamide | 0.25 (.071–0.883) | 25 |

We claim:

1. A compound of the formula:

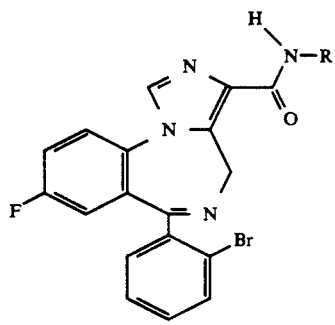

wherein R is hydrogen, CH$_3$CH$_2$—, CH$_2$=CH—CH$_2$—, (CH$_3$)$_2$CH—, CH$_3$CH$_2$CH$_2$— or

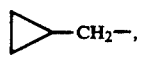

or a pharmaceutically acceptable salt thereof.

2. The compound according to claim 1, wherein the compound is 6-(2-bromophenyl)-N-ethyl-8-fluoro-4H-imidazo[1,5-a][1,4]benzodiazepine-3-carboxamide.

3. The compound according to claim 1, wherein the compound is 6-(2-bromophenyl)-8-fluoro-N-(2-propenyl)-4H-imidazo[1,5-a][1,4]benzodiazepine-3-carboxamide.

4. The compound according to claim 1, wherein the compound is 6-(2-bromophenyl)-8-fluoro-N-propyl-4H-imidazo[1,5-a][1,4]benzodiazepine-3-carboxamide.

5. The compound according to claim 1, wherein the compound is 6-(2-bromophenyl)-8-fluoro-N-(1-methylethyl)-4H-imidazo[1,5-a][1,4]benzodiazepine-3-carboxamide.

6. A method of treating panic disorders in a host comprising administering to the host in need of such treatment an effective antipanic amount of a compound of the formula:

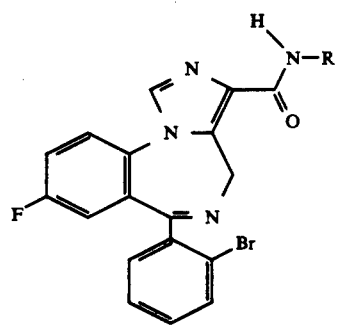

wherein R is hydrogen, CH$_3$CH$_2$—, CH$_2$=CHCH$_2$—, (CH$_3$)$_2$CH—, CH$_3$CH$_2$CH$_2$—, or

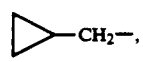

or a pharmaceutically acceptable salt thereof.

7. The method according to claim 6 comprising administering an effective amount of 6-(2-bromophenyl)-N-ethyl-8-fluoro-4H-imidazo[1,5-a][1,4]benzodiazepine-3-carboxamide.

8. The method according to claim 6 comprising administering an effective amount of 6-(2-bromophenyl)-8-fluoro-N-(2-propenyl)-4H-imidazo[1,5-a][1,4]benzodiazepine-3-carboxamide.

9. The method according to claim 6, comprising administering an effective amount of 6-(2-bromophenyl)-8-fluoro-N-propyl-4H-imidazo[1,5-a][1,4]benzodiazepine-3-carboxamide.

10. The method according to claim 6, comprising administering an effective amount of 6-(2-bromophenyl)-8-fluoro-N-(1-methylethyl)-4H-imidazo[1,5-a][1,4]benzodiazepine-3-carboxamide.

11. A method of treating epileptic disorders in a host comprising administering to a host in need of such treatment, an effective antiepileptic amount of a compound of the formula:

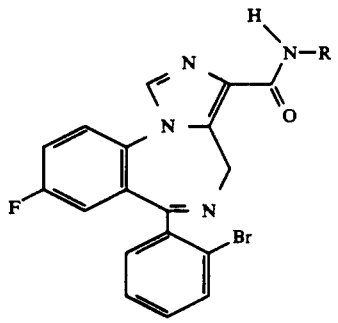

wherein R is hydrogen, CH$_3$CH$_2$—, CH$_2$=CHCH$_2$—, (CH$_3$)$_2$CH—, CH$_3$CH$_2$CH$_2$—, or

or a pharmaceutically acceptable salt thereof.

12. The method according to claim 11 comprising administering an effective amount of 6-(2-bromophenyl)-N-ethyl-8-fluoro-4H-imidazo[1,5-a][1,4]benzodiazepine-3-carboxamide.

13. The method according to claim 11 comprising administering an effective amount of 6-(2-bromophenyl)-8-fluoro-N-(2-propenyl)-4H-imidazo[1,5-a][1,4]benzodiazepine-3-carboxamide.

14. The method according to claim 11 comprising administering an effective amount of 6-(2-bromophenyl)-8-fluoro-N-propyl-4H-imidazo[1,5-a][1,4]benzodiazepine-3-carboxamide.

15. The method according to claim 11 comprising administering an effective amount of 6-(2-bromophenyl)-8-fluoro-N-(1-methylethyl)-4H-imidazo[1,5-a][1,4]benzodiazepine-3carboxamide.

16. A pharmaceutical composition which comprises an effective amount of the compound according to claim 1; and a pharmaceutically acceptable carrier.

17. The compound 6-(2-bromophenyl)-N-[(cyclopropyl)methyl]-8-fluoro-4H-imidazo[1,5-a][1,4]benzodiazepine-3-carboxamide; or a pharmaceutically acceptable salt thereof.

18. A method of treating panic disorders in a host comprising administering to said host in need of such treatment, an effective antipanic amount of the compound of claim 17.

19. A method of treating epileptic disorders in a host comprising administering to said host in need of such treatment an effective antiepileptic amount of the compound of claim 17.

20. The compound 6-(2-bromophenyl)-8-fluoro-4H-imidazo[1,5-a][1,4]benzodiazepine-3-carboxamide; or a pharmaceutically acceptable salt thereof.

21. A method of treating panic disorders in a host comprising administering to said host in need of such treatment, an effective antipanic amount of the compound of claim 20.

22. A method of treating epileptic disorders in a host comprising administering to said host in need of such treatment an effective antiepileptic amount of the compound of claim 20.

23. A pharmaceutical composition which comprises an effective amount of the compound according to claim 17; and a pharmaceutically acceptable carrier.

24. A pharmaceutical composition which comprises an effective amount of the compound according to claim 10; and a pharmaceutically acceptable carrier.

* * * * *